(12) United States Patent
Mabratu

(10) Patent No.: US 6,537,564 B1
(45) Date of Patent: Mar. 25, 2003

(54) ALL NATURAL HAIR RELAXER AND CONDITIONER

(76) Inventor: Maza Mabratu, 895 Main St., Apt. 11, Hackensack, NJ (US) 07601

( * ) Notice: Subject to any disclaimer, the term of this patent is extended or adjusted under 35 U.S.C. 154(b) by 0 days.

(21) Appl. No.: 10/063,090

(22) Filed: Mar. 18, 2002

(51) Int. Cl.⁷ .............................. A61K 7/00; A61K 7/06; A61K 7/075; A61K 35/78
(52) U.S. Cl. .................. 424/401; 424/70.1; 424/70.27; 424/725
(58) Field of Search ................................ 424/401, 70.1, 424/70.27, 725

(56) References Cited

U.S. PATENT DOCUMENTS 6,342,208 B1 * 1/2002 Hyldgaard et al.
6,372,234 B1 * 4/2002 Deckers et al.

* cited by examiner

Primary Examiner—Thurman K. Page
Assistant Examiner—Simon J. Oh
(74) Attorney, Agent, or Firm—Richard A. Joel, Esq.

(57) ABSTRACT

A hair relaxer and conditioner consisting of natural components such as coffee, walnut oil, fish oil carnauba milk and honey. The components are mixed in predetermined proportions to provide hair straightening without damage to the hair and scalp. The pH of the product is between 4.70 and 5.30.

2 Claims, No Drawings

ALL NATURAL HAIR RELAXER AND CONDITIONER

BACKGROUND OF INVENTION

This invention relates to hair relaxers and conditioners and particularly to a new and improved product that includes fish oil with cholesterol and walnut oil with cholesterol along with other ingredients such as coffee carnauba, milk and honey.

A number of patents exist in the prior art but they are mainly concerned with the combination of an alkali metal hydroxide and an organic base to provide an effective hair straightener.

Among the prior art patents are U.S. Pat. No. 4,911,919 to Patel, et al which discloses a hair straightening conditioner consisting essentially of effective amounts of a nonionic water-soluble cellulose polymer, polyvinyl pyrrolidone, a di-$C_{10}$–$C_{22}$ alkyl di-$C_1$–$C_3$ C alkyl quaternary ammonium compound, a $C_8$–$C_{18}$ alkylamido $C_2$–$C_3$ alkyl di-$C_1$–$C_3$ alkyl amine, propylene glycol, mineral oil, a $C_8$–$C_{18}$ alkanol and cyclomethicone in an aqueous vehicle having a pH of 4 to 6. This provides a stable composition having straightening properties as well as conditioning properties including good body, luster, combability and strengthening of hair.

U.S. Pat. No. 5,679,327 to Darkwa, et al, discloses an improved highly alkaline hair straightening emulsion of a strong nitrogenous organic base and alkali metal hydroxide in the presence of an alkaline earth metal cation.

U.S. Pat. No. 5,639,449 to Syed, et al, discloses hair straightening, relaxing compositions with alkali metal hydroxides comprising the relaxing element. The patent discloses the use of a hair swelling component and a cationic polymer effective to strengthen the hair.

Other patents of interest include U.S. Pat. No. 4,898,726 to Beste and U.S. Pat. No. 5,641,478 to Syed, et al. The problem with these patents is the possibility of negative hair conditioning problems associated with the strong hydroxide and other compounds. The present invention utilizes natural compounds in particular proportions to provide the conditioning as well as hair relaxing that the consumer desires.

SUMMARY OF INVENTION

This invention relates to hair relaxers and conditioners and particularly to a hair conditioner and relaxer using coffee, walnut oil, fish oil, carnauba milk, alcohol, honey, aloe vera gel, quaternium 15, methlyparaben, propylparaben, and fragrance in proportions determined to enhance the characteristics of the invention. The use of natural compounds straightens the hair while conditioning it. The use of harmful alkali metal hydroxides is often damaging both to the hair and scalp. Nevertheless, conventional hair straightening products usually include such compounds.

Accordingly, an object of this invention is to provide a new and improved hair straightening and conditioning composition.

Another object of this invention is to provide a new and improved hair straightening and conditioning product that includes natural compounds.

A further object of this invention is to provide a new and improved hair straightening and relaxer including coffee, walnut oil, carnauba milk, fish oil, walnut oil, alcohol and honey.

A more specific object of this invention is to provide a new and improved hair straightener and conditioner comprising particular proportions of distilled water, with natural oils, alcohol, honey, aloe vera gel, methlyparaben, propylparaben, coffee and a fragrance.

DETAILED DESCRIPTION

The invention relates to hair straightening and conditioning compositions and particularly to compositions including natural compounds. The prior art methods of using hot irons or metal alkali hydroxides and acids to straighten hair are objectionable because of the damage that they inflict upon one's hair and often their scalp.

It has been found that the use of particular natural compounds in predetermined proportions achieves a straightening effect while simultaneously conditioning the hair. Among the primary components of the subject relaxer and conditioner are coffee that is in a solution with distilled water. The walnut oil and commonly available fish oil are mixed with carnauba milk and acetyl alcohol and combined with the coffee.

Finally, in smaller amounts, honey, aloe vera gel, quanternium 15, methlyparaben, propylparaben and fragrance are added. The particular proportions by weight are shown on the chart below:

PERCENT WEIGHT INGREDIENTS.
44.75 DISTILLED WATER.
18.00 COFFEE.
20.00 WALNUT OIL.
5.00 FISH OIL.
5.00 CARNAUBA MILK.
5.00 ACETYL ALCOHOL.
0.25 HONEY.
0.50 ALOE VERA GEL.
0.20 QUATERNIUM 15.
0.10 METHLYPARABEN.
0.20 PROPYLPARABEN.
1.00 FRAGRANCE.

The resulting composition has a pH of 4.70 to 5.30 rather than the high pH of the prior art products. Notably, the main ingredients of the composition are coffee and walnut oil that make up 82.75 percent by weight. Fish oil, carnauba milk and acetyl alcohol each are 5 percent by weight bringing the total to 97.75 percent. The addition of a fragrance 1 percent by weight brings the total up to 98.75 percent and the addition of aloe vera gel 1 percent by weight to promote the handling of the composition brings the total amount up to 99.75 percent by weight. Small amounts of quaternium 15 (0.2 percent) methlyparaben (0.10 percent) and propylparaben (0.2 percent) are added to stabilize the ingredients.

The natural ingredients of coffee walnut oil, fish oil, carnauba milk with an acetyl carrier combine with kinky hair to relax it. After applying the composition to the hair, a comb is run through the hair to spread the composition and relax the kinky hair into a straightened condition. The hair relaxes rather than entering into a chemical reaction which might destroy the hair.

The addition of honey and aloe vera gel condition the relaxed hair to add luster. The fragrance is necessary to overcome whatever mild scents the other ingredients have and to make the composition attractive to the consumer.

The composition has successfully completed trials that testify to the fact that this all natural treatment for hair leaves the hair soft, smooth and relaxed. The composition also stimulates hair follicles to promote hair growth. Curly, kinky or frizzy hairs are substantially eliminated. A small amount of the chemical free relaxer is applied to the hair and scalp before bedtime to attain best results.

While the invention has been explained by a detailed description of certain specific embodiments, it is understood that various modifications and substitutions can be made in any of them within the scope of the appended claims, which are intended also to include equivalents of such embodiments.

What is claimed is:

1. A hair straightening and relaxing composition comprising the following compositions by weight, distilled water 44.75 percent, coffee 18.00 percent, walnut oil 20.00 percent, fish oil 5.00 percent, carnauba milk 5.00 percent, acetyl alcohol 5.00 percent, honey 0.25 percent, aloe vera gel 0.50 percent, quaternium 15 0.20 percent, methlyparaben 0.10 percent, propylparaben 0.20 percent, and fragrance 1.00 percent.

2. A hair straightening and relaxing composition in accordance with claim 1 wherein:

the composition has a pH between 4.7 and 5.30.

* * * * *